US012708336B2

(12) United States Patent
Maur et al.

(10) Patent No.: US 12,708,336 B2
(45) Date of Patent: Aug. 18, 2026

(54) APPARATUS AND METHOD FOR THE GENERATION OF DENTAL IMAGES WITH HEIGHT-SPECIFIC DOSE APPLICATION

(71) Applicant: DENTSPLY SIRONA Inc., York, PA (US)

(72) Inventors: Susanne Maur, Bensheim (DE); Stefan Eichner, Heidelberg (DE)

(73) Assignee: Dentsply Sirona Inc., York, PA (US)

( * ) Notice: Subject to any disclaimer, the term of this patent is extended or adjusted under 35 U.S.C. 154(b) by 93 days.

(21) Appl. No.: 18/712,547

(22) PCT Filed: Nov. 23, 2022

(86) PCT No.: PCT/EP2022/083028
§ 371 (c)(1),
(2) Date: May 22, 2024

(87) PCT Pub. No.: WO2023/094474
PCT Pub. Date: Jun. 1, 2023

(65) Prior Publication Data

US 2025/0017546 A1 Jan. 16, 2025

(30) Foreign Application Priority Data

Nov. 26, 2021 (EP) .................................... 21210851

(51) Int. Cl.
*A61B 6/03* (2006.01)
*A61B 6/00* (2006.01)
(Continued)

(52) U.S. Cl.
CPC ................ *A61B 6/51* (2024.01); *A61B 6/032* (2013.01); *A61B 6/4007* (2013.01);
(Continued)

(58) Field of Classification Search
None
See application file for complete search history.

(56) References Cited

U.S. PATENT DOCUMENTS 6,553,095 B2 * 4/2003 Rinaldi .................. A61B 6/544 378/108
7,103,141 B2 * 9/2006 Sonobe ................ A61B 6/4429 378/108
(Continued)

FOREIGN PATENT DOCUMENTS

CA 3239222 6/2023
CN 118317738 7/2024
(Continued)

OTHER PUBLICATIONS

International Search Report; PCT/EP2022/083028; Feb. 20, 2023 (completed); Mar. 1, 2023 (mailed).
(Continued)

*Primary Examiner* — Thomas R Artman
(74) *Attorney, Agent, or Firm* — SCHWEGMAN LUNDBERG & WOESSNER, P.A.

(57) ABSTRACT

An extraoral dental X-ray apparatus for imaging of a patient in the dental region including: a radiator array having at least two individual radiators each for emitting X-rays, and offset at least along a predetermined direction (z); and an X-ray detector for at least partially detecting the X-rays emitted by the individual radiators, the radiator array and the X-ray detector being rotatably arranged about an axis parallel to said predetermined direction, further including a control device for separately controlling the individual radiators, the control device being configured such that the emitted X-rays of the at least two individual radiators differ in intensity and/or spectral distribution of the X-rays to effect an intensity and/or spectral distribution which can be varied along
(Continued)

the predetermined direction. The control device can adaptively adapt the intensity and/or spectral distribution to the anatomy of the patient.

17 Claims, 2 Drawing Sheets

(51) Int. Cl.
*A61B 6/40* (2024.01)
*A61B 6/42* (2024.01)
*A61B 6/51* (2024.01)

(52) U.S. Cl.
CPC .......... *A61B 6/4035* (2013.01); *A61B 6/4085* (2013.01); *A61B 6/4233* (2013.01); *A61B 6/4441* (2013.01); *A61B 6/482* (2013.01); *A61B 6/488* (2013.01); *A61B 6/544* (2013.01)

(56) References Cited

U.S. PATENT DOCUMENTS

| | | | | |
|---|---|---|---|---|
| 7,486,759 | B2 * | 2/2009 | Suzuki | A61B 6/51<br>378/38 |
| 10,405,813 | B2 * | 9/2019 | Jouhikainen | A61C 19/04 |
| 11,020,071 | B2 * | 6/2021 | Sa | A61B 6/42 |
| 2002/0085673 | A1 | 7/2002 | Rinaldi | |
| 2003/0007602 | A1 * | 1/2003 | Sonobe | A61B 6/51<br>378/207 |
| 2008/0137802 | A1 * | 6/2008 | Suzuki | A61B 6/51<br>378/4 |
| 2016/0220207 | A1 * | 8/2016 | Jouhikainen | A61B 6/4035 |
| 2021/0030382 | A1 * | 2/2021 | Sa | A61B 6/4435 |
| 2025/0017546 | A1 * | 1/2025 | Maur | A61B 6/51 |

FOREIGN PATENT DOCUMENTS

| | | | | |
|---|---|---|---|---|
| EP | 2198783 | A1 | 6/2010 | |
| EP | 2387945 | A1 * | 11/2011 | A61B 6/583 |
| EP | 2609861 | A1 * | 7/2013 | A61B 6/03 |
| EP | 3053525 | A2 | 8/2016 | |
| EP | 3564022 | A1 | 11/2019 | |
| EP | 3654022 | | 5/2020 | |
| EP | 4186435 | | 5/2023 | |
| EP | 4436485 | | 10/2024 | |
| JP | 2007319575 | A * | 12/2007 | |
| JP | 2024542581 | | 11/2024 | |
| KR | 20240112306 | | 7/2024 | |
| WO | WO-2008035828 | A1 * | 3/2008 | A61B 6/032 |
| WO | 2023094474 | | 6/2023 | |

OTHER PUBLICATIONS

Written Opinion of the International Searching Authority; PCT/EP2022/083028; Feb. 20, 2023 (completed); Mar. 1, 2023 (mailed).

"European Application Serial No. 21210851.8, Extended European Search Report mailed May 9, 2022", 9 pgs.

"European Application Serial No. 21210851.8, Response filed Nov. 30, 2023 to Extended European Search Report mailed May 9, 2022", 31 pgs.

"Japanese Application Serial No. 2024-531351, Voluntary Amendment filed Jul. 25, 2024", W English Claims, 10 pgs.

"International Application Serial No. PCT EP2022 083028, International Preliminary Report on Patentability mailed Jun. 6, 2024", 7 pgs.

* cited by examiner

APPARATUS AND METHOD FOR THE GENERATION OF DENTAL IMAGES WITH HEIGHT-SPECIFIC DOSE APPLICATION

CROSS-REFERENCE TO RELATED APPLICATIONS

This is a National Phase application of International Application No. PCT/EP2022/083028, filed Nov. 23, 2022, which claims the benefit of and priority to European Application Ser. No. 21210851.8, filed on Nov. 26, 2021, which are herein incorporated by reference for all purposes.

TECHNICAL FIELD OF THE INVENTION

The present invention relates to an X-ray apparatus for PAN, CEPH and/or DVT in the dental field.

BACKGROUND OF THE INVENTION

Extraoral dental X-ray systems usually use constant beam parameters, both per projection image and also during the rotation. Due to the patient anatomy, this leads to image regions with high and low signal components in the X-ray projections. As a result, the X-ray detectors are sometimes used in an unfavorable dose range, resulting in saturation effects in the high dose range and non-linearities in the low dose range of the X-ray detector. X-ray detectors are usually not able to adequately detect the given intensity dynamics.

In general, the physician decides on the radiation parameters according to experience, depending on the patient and the indication. The ALARA (As Low As Reasonably Achievable) principle should be applied here. Some extraoral dental X-ray systems use scout images to adapt the imaging region to the patient. Scout images can also be used for initial dose estimation and adjustment. However, scout images represent an additional effort in the imaging workflow. Some extraoral dental X-ray systems adjust the radiation parameters during the rotation to apply an increased dose in the spine region. In general, a kV increase is often applied in the spine region for panoramic imaging (PAN).

SUMMARY OF THE INVENTION

The inventors are currently unaware of any technique that allows for targeted adaptive height-specific adjustment of radiation parameters with respect to the patient anatomy. The known techniques also do not allow for anatomy-specific height-specific dose application during rotation. Anatomy-specific dose application is usually not possible in the prior art. Thus, too much dose is often applied because the height-specific, anatomy-dependent absorption behavior of the patient's head is not taken into account and the choice of radiation parameters is usually determined on the basis of the strongly absorbing anatomical structures.

For DVT and PAN imaging, there is usually an automatic dose adjustment to the patient by a scout scan or a readjustment of the radiation parameters, although these are not height-specific.

An objective of the present invention is to provide an apparatus and method for producing dental imaging (DVT, PAN and/or CEPH) with height-specific dose application.

The extraoral dental X-ray apparatus according to the invention is for imaging a patient. It comprises a radiator array having at least two individual radiators each for emitting X-rays, offset at least along a predetermined direction; and an X-ray detector for at least partially detecting the X-rays emitted by the individual radiators, the radiator array and the X-ray detector being rotatably arranged for movement about an axis parallel to the predetermined direction; wherein it further comprises a control device for separately controlling the individual radiators, the control device being adapted such that the emitted X-rays of the at least two individual radiators differ in intensity and/or spectral distribution of the X-rays in order to effect an intensity and/or spectral distribution which can be varied along the predetermined direction, wherein the control device can adapt the intensity and/or spectral distribution adaptively to the anatomy of the patient.

The advantages of the present invention are an improvement in image quality due to improved contrast imaging in the high and low dose ranges, which results from more favorable use of the dynamic range of the X-ray detector. In addition, the overall dose of the imaging can be reduced because the dose can be minimized in less absorbent anatomical regions or less relevant image regions. This does not require an additional imaging such as the scout scan, which simplifies the operation of the X-ray apparatus and saves time. Anatomy-specific dose adjustment results in reliable image quality by compensating for varying patient positioning and unfavorable structural overlays. This results in fewer repeat imaging and thus less dose application for the patient and simplified operation of the X-ray apparatus for the user.

The anatomy-specific dose adjustment can also be realized, for example, via sequential or simultaneously controlled individual radiators, via the additional use of one or more aperture devices and/or filter devices. In addition, the intensity and/or spectral distribution of the X-rays can preferably be actively readjusted during the imaging as a function of the signal from the X-ray detector. In addition, the operating mode of the X-ray detector can be actively adjusted.

The X-ray imaging parameters are, for example, predefined or selectively configurable by the user. The imaging parameters (i.e., configuration variables) include the desired imaging method, the target value for intensity and/or spectral distribution of the X-rays, the collimation by the aperture devices, the size and/or location of the imaging region in the patient's head, the trajectory of the radiator array and the X-ray detector, etc.

BRIEF DESCRIPTION OF THE DRAWINGS

In the following description, the present invention will be explained in more detail with reference to the exemplary embodiments and with reference to the drawings, wherein.

DETAILED DESCRIPTION OF THE INVENTION

Figure 1:
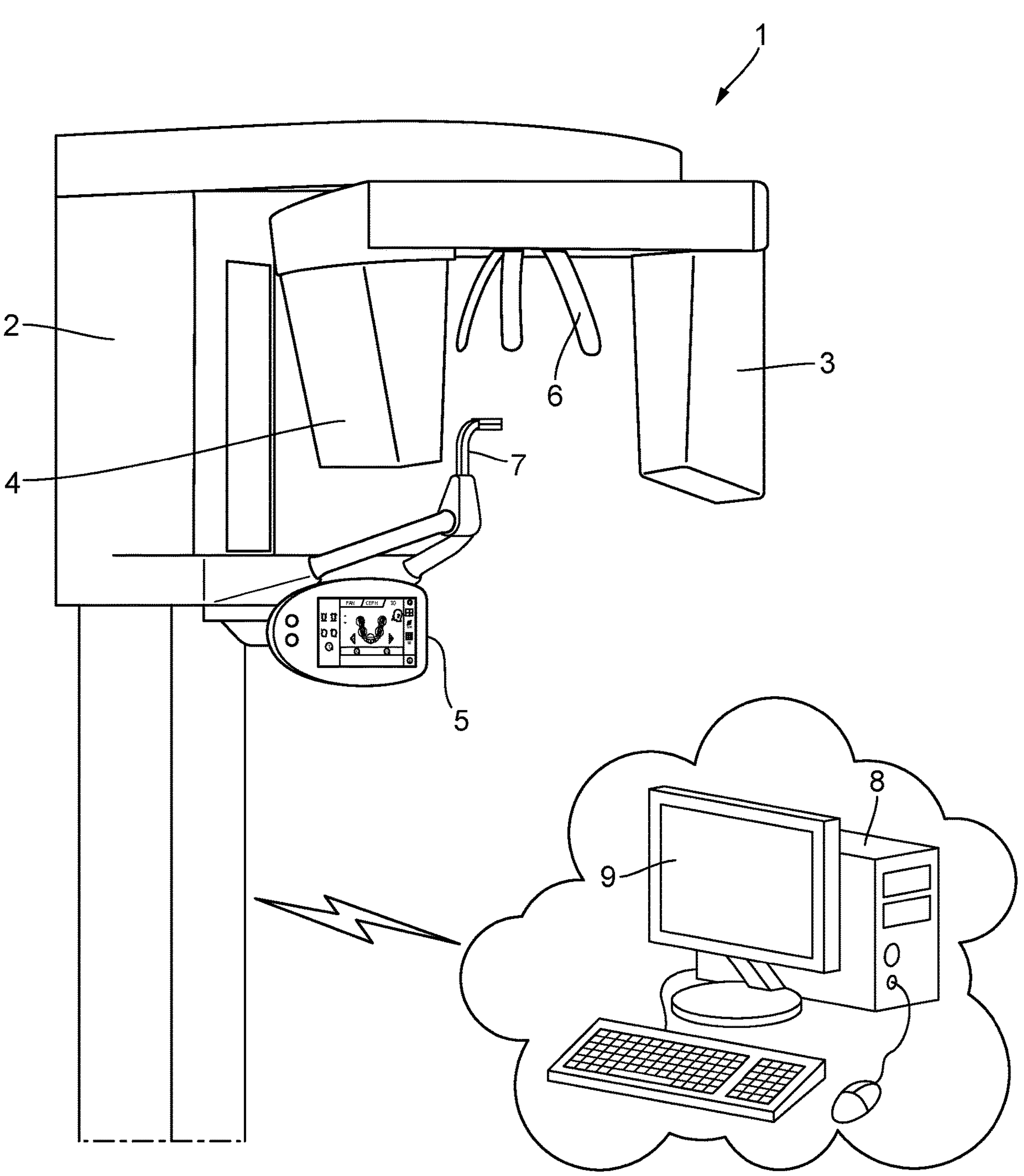
FIG. 1—shows a schematic drawing of a computerized DVT system according to an embodiment.

The reference numbers shown in the drawings designate the elements listed below, which are referred to in the following description of exemplary embodiments.

1. DVT system
2. Extraoral X-ray apparatus
3. Radiation array
3-1 X-ray individual radiator
3-2 X-ray individual radiator
4. X-ray detector
5. Control unit

6. Head fixation
7 Bite block
8 Computing unit (Computer)
9. Display
10. Object of measurement or Patient head
11. Jaw arch
12. Beam cone for individual radiator
12'. Beam cone for individual radiator.
S Overlap area
Z Predetermined direction
Z Parallel axis FIG. 1 shows an embodiment example for a computer-aided DVT system (1) according to the invention. The DVT system (1) has an extraoral dental X-ray apparatus (2). In this regard, the present invention also includes a computer program having computer-readable code. The computer program may be provided on a storage medium. The extraoral dental X-ray apparatus (2) is used to perform patient imaging, generating the 2D X-ray images or sinogram. For this purpose, the X-ray apparatus (2) has an X-ray radiation array (3) and an X-ray detector (4), which are rotated around the patient's head at a constant or variable speed, respectively, during the exposure. The radiator array (3) consists of several small, fast-switchable individual radiators (3-1;3-2), which are spatially distributed and individually controllable. This allows the creation of X-ray projections from different projection angles without apparatus movement. The individual radiators (3-1;3-2) of the radiator array (3) may comprise, for example, cold cathode tubes made of, for example, carbon nanotubes. The x-ray apparatus (2) has a rotating mechanism. The trajectory of the radiation array (3) and the X-ray detector (4) during imaging may describe a circular path. Alternatively, it may assume a shape deviating from this. The X-ray source array (3) will be explained in more detail later.

The X-ray apparatus (2) further comprises a control unit (5) for operating or configuring the same. As shown in FIG. 1, a patient can be positioned in the X-ray apparatus (1) with the bite block (7) and the head fixation (6). The DVT system (1) further comprises, preferably a computer (8) or a computing unit that can be connected to the X-ray apparatus (2), and preferably a display (9), inter alia to visualize the generated data sets. The bite block (7) and the head fixation (6) serve as a device (6,7) for positioning the patient. The computer (8) can be connected to the X-ray apparatus (2) via a local network (not shown) or alternatively via the Internet. The computer (8) may be part of a cloud. The computations may take place in the cloud. Alternatively, the computer (8) may be integrated into the X-ray apparatus (2). The computer (8) executes the computer program and provides the data sets, including for visualization on the display (9). The display (9) can be spatially separated from the X-ray apparatus (2). Preferably, the computer (8) can also control the X-ray apparatus (2). Alternatively, separate computers can be used for control and image reconstruction.

Figure 2:
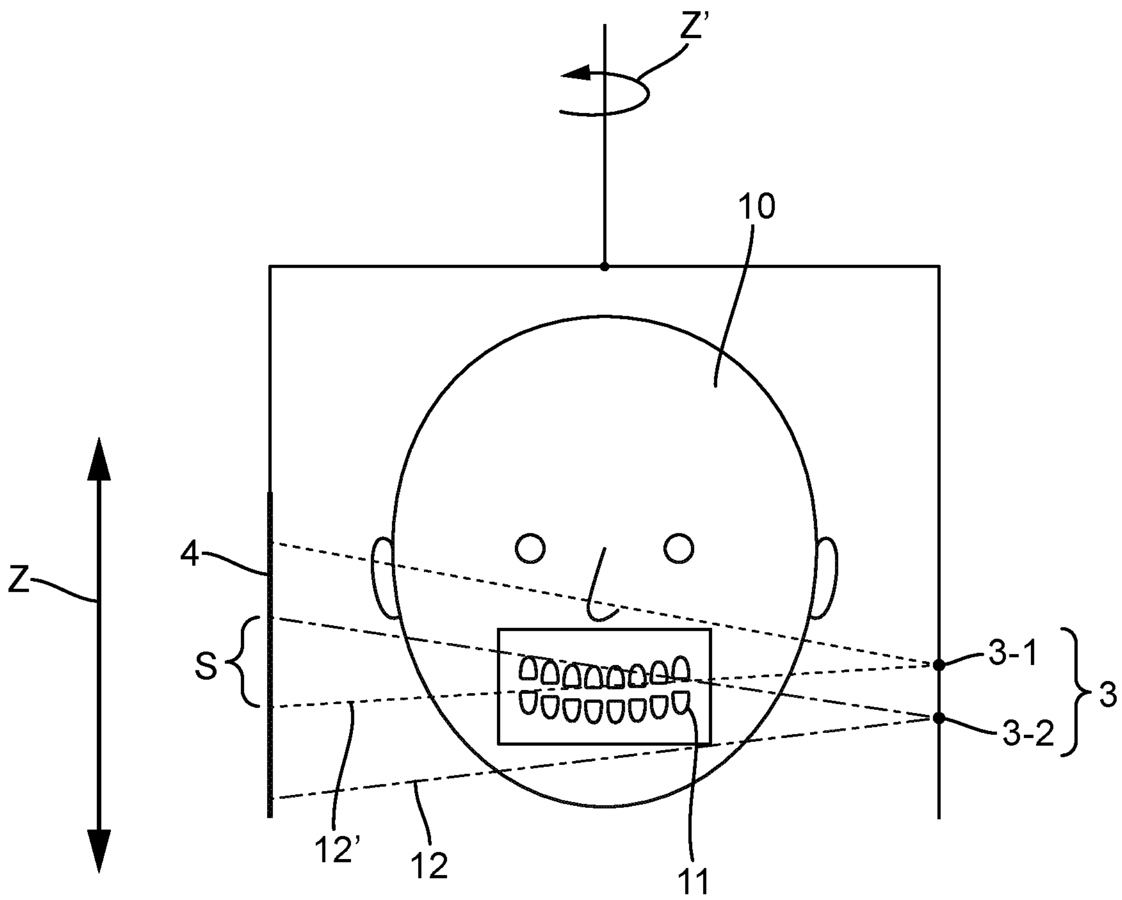
FIG. 2—shows a detailed schematic partial view of the extraoral X-ray apparatus according to an embodiment.

FIG. 2 shows a detailed schematic partial view of the X-ray apparatus (2). As shown in FIG. 2, the radiation array (3) has at least two individual radiators (3-1;3-2) each for emitting X-ray radiation, which are offset at least along a predetermined direction (z) (e.g. in the vertical direction) by a predetermined distance. The X-ray apparatus (2) can be set upright with the patient being positioned standing. Alternatively, the X-ray apparatus (2) could be set up horizontally or, preferably, diagonally over an adjustable range of angles, with the patient being positioned lying or sitting by means of a backrest. The predetermined distance is fixed but can also preferably be actively controlled. The X-ray detector (4) is designed for at least partial detection of the X-ray radiation emitted by the individual radiators (3-1; 3-2), wherein the beam cones of the individual radiators (12; 12') on the X-ray detector (4) can have an overlap area(s). For PAN and DVT, the radiation array (3) and the X-ray detector (4) are rotatably disposed about an axis (z') parallel to the predetermined direction (z). For one-shot CEPH, the X-ray detector (4) could be fixed-mounted or not rotated. For linear-CEPH, the X-ray detector (4) is additionally displaceably disposed. Alternatively, an additional X-ray detector (not shown) on a cantilever arm could be used for CEPH. The mechanical configuration for displacement of the X-ray detector in the CEPH modality is optional to PAN or DVT modality. The X-ray apparatus (2) may be a combination unit for PAN, DVT, and CEPH or may support only one or two of the above modalities. The X-ray apparatus (1) comprises a control device (not shown) for separately controlling the individual radiators (3-1;3-2), wherein the control device is configured such that the emitted X-ray beams of the at least two individual radiators (3-1;3-2) differ in intensity and/or spectral distribution of the X-ray beams in order to cause an intensity and/or spectral distribution variable along the predetermined direction (z). The control comprises the separate regulation of the current and/or voltage to the respective single radiator (3-1;3-2). Thus, a height-specific dose application can be actively enabled.

In one embodiment, the intensity and/or spectral distribution of the X-ray radiations of the individual radiators is varied during the movement of the apparatus (e.g., by varying current and/or voltage). This has the advantage that saturation effects in the high dose range and non-linearities in the low dose range of the X-ray detector can be reduced depending on the projection angle.

In an advantageous embodiment, the control device is configured such that the individual radiators (3-1;3-2) can be activated sequentially or simultaneously, and the detected signals of the X-ray detector (4) are read out synchronously with the activation of the individual radiators (3-1;3-2). During the sequential control of the individual radiators, the signals of the X-ray detector can be read out separately for each individual radiator and thus ambiguities in the overlap area(s) in the reconstruction can be avoided. During the simultaneous control of the individual emitters, the signals of the X-ray detector can be read out simultaneously for several individual emitters. Thereby, a lower readout rate of the X-ray detector can be used, which allows a longer integration time of the X-ray beams and reduces non-linearities in the low-dose range.

In an advantageous embodiment, the individual radiators (3-1; 3-2) each have their own aperture device for collimating the X-ray radiation. This has the advantage that the beam cones of the individual radiators (12; 12') can be better delimited from one another and the overlap area(s) of the individual emitters can be minimized and better defined. Alternatively, or additionally, the radiator array (3) has a common aperture device. The aperture device can be implemented by a fixed aperture or a mechanically motorized variable aperture. The aperture device has the advantages that the radiation exposure for the patient is minimized, the scattered radiation is reduced, and the active usable area of the X-ray detector is not over-radiated.

In a further advantageous embodiment, the individual radiators (3-1;3-2) each have their own filter device. This filter device is used for pre-filtering, or attenuation, of the X-ray radiation and for changing the X-ray spectrum. The filter device is a permanently installed filter or a mechanically motorized variable filter device such as a filter wheel with different filter materials. For example, the filter device includes filter materials such as copper or aluminum. The filter device enables, for example, a hardening of the X-ray radiation, which leads to a better representation of the bone structures. In addition, the proportion of soft X-ray radiation in the X-ray spectrum is reduced, which contributes little to the visualization of the bone and tooth structures, but represents a harmful radiation exposure for the patient. If each individual radiator (3-1;3-2) has its own filter device, for example, the filter device can be adapted to the intensity and/or spectral distribution of the X-ray radiations of the individual radiators. Alternatively, the radiation array (3) has a common filter device which filters the X-ray radiation of all individual radiators together, independent of the adapted intensity and spectral distribution of the individual radiators. Thereby, for example, a general beam hardening can be realized.

In a further advantageous embodiment, the mode of operation of the X-ray apparatus (2) can be configured by the user by means of an input device or the operating unit (5) with regard to at least one of the following configuration variables:

- Imaging methods, such as PAN, CEPH or DVT
- Target value for intensity and/or spectral distribution of the X-rays, which are taken into account during the variation, for example as a target value for a maximum value or an average value,
- Collimation by the aperture devices, for example, on the maxillary or mandibular region,
- Size and/or position of the imaging area in the patient's head, for example to restrict it to the left or right side of the jaws or selected anatomical structures,
- Trajectory of the radiation array (3) and the X-ray detector (4), for example to reduce image artifacts, wherein the control device is further configured to control the individual radiators based on the user configuration.

In a further advantageous embodiment, the control device is further configured to control the individual radiators for the imaging such that the intensity and/or spectral distribution of the X-ray radiation is adaptively adapted to the anatomy of the patient. This has the advantage of reducing saturation effects in the high dose range and non-linearities in the low dose range of the X-ray detector. In addition, in dose-sensitive anatomical regions, such as the orbits, the dose load to the patient can be reduced. In addition, in highly absorbing anatomical structures, such as the bony or metallic structures, increased intensity and/or adjusted spectral distribution can be applied to avoid non-linearities of the X-ray detector in the image regions with high absorption. Wherein, the control device determines the patient's anatomy according to at least one of the following:

(a) based on general assumptions about human anatomy such as empirical biometric data, (b) based on the setting of a device for positioning the patient, e.g., the height of the patient or the thickness of the patient's skull may be inferred via the position of the bite block or the head fixation, (c) based on the pre-know anatomy of the patient, such as using a scout image, an optical surface model, or another existing image data set (PAN, CEPH, 3D) of the same patient. The position, or height, of the radiator array and X-ray detector is preferably adjustable and known to the X-ray apparatus. Knowledge of the pre-known anatomy of the specific patient can be stored in or retrieved from a database.

In a further advantageous embodiment, the control device is further configured to control the individual radiators for the imaging in such a way that the intensity and/or spectral distribution of the X-ray beams are readjusted during the imaging as a function of the signal from the X-ray detector. The aim of this is to avoid too low and too high signals at the X-ray detector in order to reduce saturation effects in the high dose range and non-linearities in the low dose range of the X-ray detector and to operate the X-ray detector in a linear operating range as much as possible.

In another embodiment, the rotational speed of the X-ray detector (4) and the radiation array (3) is varied during the imaging. While keeping the intensity and spectral distribution constant, the total applied dose can be increased by decreasing the rotation speed or vice versa. Thus, the dose applied to a particular local structure can be controlled in addition to the previously described possibilities.

In a further advantageous embodiment, the control device is further configured to control at least one single emitter during the imaging such that the intensity and/or spectral distribution of the X-ray radiation of the individual radiator are varied according to a predetermined sequence having a frequency of at least 50 Hz. The amplitude may depend on the patient anatomy or the measured signal at the X-ray detector. The reconstruction software computes the individual projections of the individual radiators in such a way that structures are well imaged in both the low and high dose ranges. This enables images with high contrast, especially for X-ray detectors with small dynamic range, or low bit depth. This process is analogous to HDR imaging in digital photography.

In a further advantageous embodiment, the operating mode of the X-ray detector for the respective intensity and/or spectral distribution of the X-ray beams used is adapted completely or regionally before or during the imaging, for example in its operating mode with regard to the dynamic range, the readout rate, the readout range and/or the gain.

In a further advantageous embodiment, the extraoral X-ray apparatus (2) comprises one or more of the PAN, CEPH, DVT imaging methods, wherein these are selectable by the user.

According to the method of the invention, a common image for PAN/CEPH or a volume for DVT is calculated from signals of the X-ray detector (4) of the extraoral dental X-ray apparatus (2), taking into account the information of the control of the individual radiators (3-1-; 3-2) in the respective imaging method.

The method according to the invention is implemented by the reconstruction software with computer-readable code, which can be executed by the computerized X-ray apparatus (2).

The reconstruction software is stored on a computer-readable storage medium.

The computerized DVT system (1) includes an extraoral dental X-ray apparatus (2), and a computing unit (8) configured to run the reconstruction software.

According to the present invention, the data sets generated by the above embodiments may be presented to a physician for visualization, in particular for diagnostic purposes, preferably by means of the display (9) or a printout.

Calibration

A calibration routine is also provided that calibrates the radiation array (3) together with the X-ray detector (4). The calibration routine includes the following steps, among others:

- Calibration of the dose rate of the individual radiators based on the applied current and voltage, and the beam time;

Calibration of the local radiation intensity distributions of the individual radiators on the X-ray detector plane;

Calibration of the overlap area of the individual radiators on the X-ray detector plane;

Use (optionally) of a suitable test object of measurement with one or more materials to calibrate the individual radiator specific X-ray spectra.

The invention claimed is:

1. An extraoral dental X-ray apparatus for imaging of a patient in the dental region comprising:

a radiator array having at least two individual radiators each configured to emit X-rays, which are offset at least along a predetermined direction (z); and an X-ray detector configured to at least partially detect the X-rays emitted by the individual radiators, the radiator array and the X-ray detector being rotatably arranged about an axis (z') parallel to said predetermined direction (z);

a control device that separately controls the individual radiators, the control device being configured such that the emitted X-ray beams of the at least two individual radiators differ in the intensity and/or spectral distribution of the X-rays to effect an intensity and/or spectral distribution which is varied along the predetermined direction (z), wherein the control device adapts the intensity and/or spectral distribution adaptively to the anatomy of the patient by separately regulating the current and/or voltage to each of the individual radiators to effect a height-specific dose application along the predetermined direction (z).

2. The extraoral dental X-ray apparatus according to claim 1, wherein the control device is configured such that the individual radiators can be actuated sequentially or simultaneously, and the detected signals of the X-ray detector are read out synchronously with the actuation of the individual radiators.

3. The extraoral dental X-ray apparatus according to claim 1, wherein the individual radiators each have their own aperture device, or the radiator array has a common aperture device.

4. The extraoral dental X-ray unit according to claim 1, wherein the individual radiators each have an own filter device, or the radiator array has a common filter device.

5. The extraoral dental X-ray apparatus according to claim 1, wherein a mode of operation of the X-ray apparatus is configured by the user using an input device with respect to at least one of the following configuration variables: PAN, CEPH, DVT imaging method, target value for intensity and/or spectral distribution of the X-rays, collimation by aperture devices, filtering by filter device, size and/or position of the imaging region in the patient head, trajectory of the radiator array and of the X-ray detector, and the control device is further configured to control the individual radiators on the basis of the user configuration.

6. The extraoral dental X-ray apparatus according to claim 1, wherein the control device is further configured to control the individual radiators for the imaging such that the intensity and/or spectral distribution of the X-rays are adaptively adapted to the patient's anatomy, wherein the control device determines the patient's anatomy according to at least one of the following variants:

(a) general assumptions about human anatomy, (b) adjustment of a device for positioning the patient;

(c) pre-known anatomy of the patient.

7. The extraoral dental X-ray apparatus according to claim 1, wherein the control device is further configured to control the individual radiators for the imaging such that the intensity and/or spectral distribution of the X-rays is readjusted during the imaging as a function of the signal from the X-ray detector.

8. The extraoral dental X-ray apparatus according to claim 1, wherein the control device is further configured to control at least one individual radiator during imaging such that the intensity and/or spectral distribution of the X-rays of the individual radiator are varied according to a predetermined sequence which has a frequency of at least 50 Hz.

9. The extraoral dental X-ray apparatus according to claim 1, wherein the operating mode of the X-ray detector for the respective intensity and/or spectral distribution of the X-rays used is adapted completely or regionally before or during the imaging, wherein the operating mode comprises at least one of the following parameters: dynamic range, readout rate, readout range, and the gain.

10. The extraoral dental X-ray apparatus according to claim 1, wherein the extraoral X-ray apparatus comprises one or more of the following imaging methods: PAN, CEPH, and DVT, wherein the one or more imaging methods are selectable by the user.

11. A method for reconstructing a common image for PAN/CEPH or a volume for DVT from signals of the X-ray detector of the extraoral dental X-ray apparatus according to claim 1, wherein the information of the control of the individual radiators is taken into account in the method.

12. A non-transitory computer-readable storage medium including instructions that when executed by a computer, cause the computer to perform the method of claim 11.

13. The extraoral dental X-ray apparatus according to claim 1, wherein the control device adapts the intensity and/or spectral distribution adaptively to the anatomy of the patient such that the intensity and/or spectral distribution of the X-ray beams of the individual radiators is varied during rotation of the radiator array and X-ray detector about the axis (z') based on the patient's anatomy.

14. The extraoral dental X-ray apparatus according to claim 1, wherein the control device adapts the intensity and/or spectral distribution adaptively to the anatomy of the patient such that saturation effects in a high dose range and non-linearities in a low dose range of the X-ray detector are reduced, thereby improving contrast imaging in the high and low dose ranges through more favorable use of the dynamic range of the X-ray detector.

15. The extraoral dental X-ray apparatus according to claim 1, wherein the individual radiators comprise cold cathode tubes.

16. The extraoral dental X-ray apparatus according to claim 1, wherein the control device is configured to concurrently and independently regulate the current and/or voltage supplied to each of the at least two individual radiators during imaging such that each individual radiator simultaneously emits X-rays at a respective intensity and/or spectral distribution determined by the control device based on the anatomy of the patient.

17. The extraoral dental X-ray apparatus according to claim 1, wherein the control device determines the current and/or voltage for each individual radiator based on a position of the respective individual radiator along the predetermined direction (z) relative to the anatomy of the patient such that the individual radiator offset along the predetermined direction (z) toward a more absorbing anatomical region of the patient is operated at a higher intensity and/or adjusted spectral distribution compared to the individual radiator offset toward a less absorbing anatomical region of the patient.

* * * * *